(12) United States Patent
Sperling et al.

(10) Patent No.: US 6,391,647 B1
(45) Date of Patent: *May 21, 2002

(54) METHOD AND A DEVICE FOR ATOMIC ABSORPTION SPECTROSCOPY

(75) Inventors: Michael Sperling, Sipplingen; Albert Gilmutdinov, Ueberlingen, both of (DE)

(73) Assignee: PerkinElmer Instruments LLC, Shelton, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/784,678

(22) Filed: Jan. 21, 1997

(30) Foreign Application Priority Data

Jan. 26, 1996 (DE) .......................... 196 02 801

(51) Int. Cl.⁷ .................. G01N 21/62; G01N 33/20; G01J 3/30

(52) U.S. Cl. .................. 436/171; 436/73; 436/79; 436/80; 436/81; 436/82; 436/83; 436/84; 436/164; 436/181; 436/182; 356/312; 356/319

(58) Field of Search .................. 436/73, 79–84, 436/164, 171, 181, 182, 183; 356/312, 319, 326, 331

(56) References Cited

FOREIGN PATENT DOCUMENTS

| EP | 0182259 | 5/1986 |
| EP | 0274134 | 7/1988 |
| EP | 0291660 | 11/1988 |
| EP | 0411481 | 2/1991 |
| WO | 9423285 | 10/1994 |

OTHER PUBLICATIONS

D. D. Siemer et al, Appl. Spectrosc. 1984, 38, 389–391, Mar. 1984.*
C. L. Chakrabarti et al, Spectrochim. Acta 1985, 40B, 1663–1676, Oct. 1985.*
D. C. Baxter et al, Spectrochim. Acta 1987, 42B, 1005–1010, Aug. 1987.*
M. Sperling et al, Spectrochim. Acta 1996, 51B, 897–930, Jul. 1996.*
A.K. Gilmutdinov et al. *Spectrochim. Acta 1984, 39B*, 171–192.*
R.J. Lovett *Appl. Spectrosc. 1985, 39*, 778–786.*
B. Welz et al, *Spectrochim. Acta 1988, 43B*, 1187–1207.*
B.V. L'vov et al. *J. Anal, Chem. USSR. 1989, 44*, 652–657.*
B.V. L'vov *Spectrochim, Acta 1990, 45B*, 633–655.*

(List continued on next page.)

*Primary Examiner*—Arlen Soderquist
(74) *Attorney, Agent, or Firm*—St. Onge Steward Johnston & Reens LLC

(57) ABSTRACT

The present invention refers to a method for atomic absorption spectroscopy of an analyte which is contained in a sample to be analyzed and which is converted into free atoms in an absorption volume of an atomizer, said method comprising the steps of (a) position- and time-dependent measuring of the atomic absorption over the cross-section of the absorption volume and (b) simultaneous determination of surface temperatures of the atomizer. This method is characterized by the steps of (c) reconstructing the temperature field in said absorption volume on the basis of the surface temperatures determined, (d) determining position- and time-dependent numbers of particles of the absorbing atoms of the analyte on the basis of the measurements of the position- and time-dependent atomic absorption and the absorption profile that has been determined with due regard to effects influencing the line profile of the analyte and with due regard to the reconstructed temperature field, and (e) determining the time-dependent total number of the absorbing atoms of the analyte on the basis of the position- and time-dependent numbers of particles. In addition, the present invention concerns a device for carrying out this method.

27 Claims, 4 Drawing Sheets

OTHER PUBLICATIONS

A.K. Gilmutdinov et al. *Spectrochim. Acta 1992, 47B*, 1075–1095.*

A.K. Gilmutdinov et al, *J. Anal, At, Spectrom, 1993, 8*, 387–395.*

C.L. Chakrabarti et al. *Anal. Chem. 1993, 65*, 716–723.*

A.K. Gilmutdinov et al. *J. Anal. Chem. USSR 1993, 48*, 576–582.*

A.K. Gilmutdinov et al. *J. Anal. At. Spectrom. 1994, 9*, 643–650.*

J. Hertzberg et al. *Appl. Phys. B 1995, B61*, 201–205.*

A.K. Gilmutdinov et al. *Appl. Spectrosc. 1995, 49*, 413–424.*

A.K. Gilmutdinov et al. *Spectrochim, Acta 1995, 50B*, 1637–1654.*

A.K. Gilmutdinov et al. *Spectrochim. Acta 1996, 51B*, 1023–1044.*

A.K. Gilmutdinov et al. CANAS '95 Colloq. Anal. Atomspektrosk.*

1996, B. Welz ed, Bodenseeverk Perkin–Elmer, Uberlingen Germany, pp 51–60.*

Yasuda, M., Murayama, S.: Measurement of Longitudinal Atom Density Distributions in a Graphite Tube Furnace Using Coherent Forward Scattering. In: Spectrochimica Acta, vol. 36B, No. 7, 1981, S.641–647.

Chang, S.B. et. al.: Capacitive–Discharge–Heated Anisotropic Pyrolytic Graphite Furnace Used For Atomic Absorption Spectrometry. In: Analytica Chimica Acta, 176, 1985, H. 11, S.1–16, S.17–32.

Davis, L.A., Winefordner, J.D.: Evaluation of a Voigt Effect Coherent Forward Scattering Atomic Spectrometer. In: Anal. Chem. 1987, 59, S.309–S.312.

Jones, Bradley T., et.al.: Continuum Source Atomic Absorption Spectrometry in a Graphite Furnace with Photodiode Array Detection. In: Anal.Chem. 1989, 61, H.15, S.1670–1674.

* cited by examiner

METHOD AND A DEVICE FOR ATOMIC ABSORPTION SPECTROSCOPY

FIELD OF THE INVENTION

The present invention refers to a method for atomic absorption spectroscopy of an analyte which is contained in a sample to be analyzed and which is converted into free atoms in an absorption volume of an atomizer, said method comprising the steps of position- and time-dependent measuring of the atomic absorption over the cross-section of the absorption volume, and simultaneous determination of surface temperatures of the atomizer.

Furthermore, the present invention refers to a device for carrying out an atomic absorption spectroscopy, comprising a radiation source, an atomizer enclosing an absorption volume, a position- and time-resolving spectrometer for measuring the light which has been emitted by the radiation source and which has passed through the absorption volume, and a means for determining the surface temperature of the atomizer.

BACKGROUND OF THE INVENTION

Such a method and such a device are known from WO 94/23285.

This known method especially includes the step of first converting an analyte of a sample to be examined in the absorption volume of a graphite furnace into the gaseous phase in the form of free atoms. These free atoms absorb characteristic wavelengths emitted by a primary light source. The extinction of the primary radiation source in these wave-lengths caused by said free atoms is then measured in a temporally resolved manner, i.e. at specific moments of time, in dependence upon the position relative to the cross-section of the furnace.

According to this method, the position- and time-dependent extinctions are first determined for various calibration standards whose concentrations are already known. Accordingly, a connection, i.e. a calibration function, between the extinction and the concentration of the analyte observed is obtained in the sample to be measured.

For determining the concentration of an unknown sample, the position- and time-dependent extinction is, subsequently, determined, and the time-dependent concentration corresponding to the measured extinction is ascertained through the calibration function.

In this connection, non-specific radiation losses (background absorption) can be corrected by background correction methods which are normally used in the field of atomic absorption spectroscopy, such as correction with a continuum radiator, Zeemann effect background correction or correction according to the Smith-Hieftje method. In accordance with the requirements of the correction technique used, data evaluation is temporally controlled in such a way that a distinction can be made between the respective signals (e.g. non-specific absorption, total absorption, emission) coming from the atomizer. In any case, however, also the background absorption is measured in a temporally resolved manner so that correction errors caused by inhomogeneous background absorption, whose distribution can, moreover, be different from that of the atomic absorption, can be avoided, such correction errors being unavoidable in the case of the conventional atomic absorption which is not spatially resolved.

Furthermore, the surface temperature of the atomizer can be measured simultaneously in this method. Additional information on the atomization process can be obtained in this way.

According to WO 94/23285, spatially local deviations, which would result in a non-linearity of the calibration function in their entirety, are taken into account by the use of a spatially-resolving type of atomic absorption spectroscopy. Hence, many calibration measurements must be carried out in this non-linear region so as to obtain a satisfactory, reliable determination of the connection between the measured extinction of the atoms within the absorption volume and the concentration of the analyte in the sample to be measured. These spatially local deviations include, for example, the inhomogeneous distribution of the atoms in the absorption volume, the inhomogeneous distribution of the radiation intensity in the absorption volume and the temperature gradients in the absorption volume.

The method and the device according to WO 94/23285 are, however, disadvantageous insofar as spectral effects, such as Doppler broadening and pressure broadening effects, which depend on the temperature, are not taken into account.

SUMMARY OF THE INVENTION

Hence, it is the object of the present invention to improve the known method and the known device.

According to the present invention, this object is achieved by a method of the type mentioned at the beginning which is characterized by the steps of reconstructing the temperature field in said absorption volume on the basis of the surface temperatures determined, determining position- and time-dependent numbers of particles of the absorbing atoms of the analyte on the basis of the measurements of the position- and time-dependent atomic absorption and the absorption profile that has been determined with due regard to effects influencing the line profile of the analyte and with due regard to the reconstructed temperature field, and determining the time-dependent total number of the absorbing atoms of the analyte on the basis of the position- and time-dependent numbers of particles.

It follows that the method according to the present invention first reconstructs, for each predetermined time step, the temperature field over the cross-section of the absorption volume on the basis of the surface temperatures of the atomizer which are determined at the support points or support values. Accordingly, the temperature is known at any point over the cross-section of the absorption volume. With the aid of this position-dependent temperature, position-dependent absorption profiles are determined in which spectral effects, such as Doppler broadening and pressure broadening effects, have already been taken into account. These position-dependent absorption profiles can then be used for determining with the aid of absorption measurements position-dependent numbers of particles on the basis of which the total number of the absorbing atoms of the analyte can then be determined for each predetermined time step.

Due to the fact that spectral effects, such as Doppler broadening and pressure broadening effects, are directly taken into account upon determining the position-dependent numbers of particles, said position-dependent numbers of particles and, consequently, also the total number of absorbing atoms can be determined with a degree of accuracy which is much higher than that obtained by methods according to the prior art. This direct taking into account has especially the effect that systematic deviations, which are caused by the above-mentioned effects, are reduced significantly.

A further advantage of the method according to the present invention results from the fact that the experimental set-up used for carrying out the measurement only has to be taken into account upon reconstructing the temperature field in the absorption volume on the basis of the surfaces temperatures determined. When the manner in which the temperature field is to be reconstructed on the basis of the surface temperatures has been determined for a specific experimental set-up, any type of analytes can be examined by means of this set-up without any necessity of measuring calibration standards. This results in a certain degree of independence of the measurements from the set-up used in the device in question.

It follows that, in addition to an improvement of the measuring accuracy, the method according to the present invention also makes the execution of these measurements much simpler.

Measurements of the position- and time-dependent absorption are corrected in an advantageous manner with regard to the above-mentioned background absorption.

According to a special embodiment of the present method, the the position- and time-dependent particle number $N(X,t)$ can be determined from $$\int_{\Delta\lambda} d\lambda J(\lambda, X) e^{-k(\lambda,T) f N(X,t)} = 10^{-A(X,t)} \int_{\Delta\lambda} d\lambda J(\lambda, X) = \Phi(X, t)$$

where $\lambda$ is the wavelength (integration variable), $\Delta\lambda$ is a spectral bandpass of the spectrometer used for measuring the atomic absorption, $J(\lambda,X)$ is an a priori known emission profile of the primary radiation source used for measuring the atomic absorption, $k(\lambda,T)$ is an a priori known temperature-dependent absorption profile, f is the oscillator strength of a transition observed, $A(X,t)$ is the position- and time-dependent extinction, and $\Phi(X,t)$ is the position- and time-dependent intensity of the radiation of the primary radiation source which passed through the absorption volume (i.e. which was not absorbed in the absorption volume), said intensity being determined by measurement.

Due to this representation of the absorption profile, it is possible to use various physical models for the absorption profile k(,T). In this respect, empirically determined models, i.e. models which have essentially been determined on the basis of measurements, can be used on the one hand and models which are known from theory on the other. The theoretically known models can, if necessary, also be optimized with regard to the experimental conditions in question. In particular, also dependencies on further physical parameters, which influence the absorption, can be taken into account in a comparatively simple manner in this representation.

Furthermore, this method also takes into consideration a spatially inhomogeneous intensity distribution of the respective primary radiation source used. It follows that a requirement which had to be fulfilled in the field of atomic absorption spectroscopy up to now, viz. the necessity of providing a homogeneous radiation intensity over the cross-section of the absorption volume, need no longer be satisfied. Hence, it is, on the one hand, no longer necessary to satisfy this demand by providing an appropriate experimental set-up. On the other hand, the accuracy of measurements will, of course, be increased according to the present invention, since errors, which were introduced in the measurement according to the prior art due to deviations from the above demand, no longer occur.

The emission profile $J(\lambda, X)$ and the temperature-dependent absorption profile $k(\lambda, T)$ can, in an advantageous manner, be determined a priori from the following formulae:

$$J(\lambda, X) = \sum_{k=1}^{n} b_k H_k\left(\frac{\lambda - \Delta\lambda_k}{\alpha}; a_e\right) + J_s(\lambda, X)$$

$$k(\lambda, T) = \sum_{k=1}^{n} b_k H_k(\lambda - \Delta\lambda_k + \Delta\lambda_s; a).$$

Where: k is the k-th hyperfine structure component of the transition observed, $\Delta\lambda_k$ is the position of the k-th hyperfine structure component, $J_s(\lambda, X)$ is the profile of the spectral scattered light component of the primary radiation source, $\Delta\lambda_s$ is the pressure broadening of the absorption profile relative to the emission profile, $H_k(\lambda; \ldots)$ is the Voigt profile of the k-th hyperfine structure component in which the Doppler broadening and the pressure broadening are taken into account, a and $a_e$ are the ratios of the Doppler broadening and the pressure broadening component for the absorption profile and the emission profile, $\alpha$ is the factor by which the emission profile is narrower than the absorption profile, and $b_k$ are the relative standardized intensities of the individual hyperfine transitions.

In accordance with this preferred embodiment, a quasi-classical model is assumed for the absorption profile and the emission profile; in said model, the transitions taking place in an atom, including the hyperfine structure transition, can be taken into account individually. This model is taken into account by a sum of the Voigt profiles generally known in the field of spectroscopy, said Voigt profiles including a Gaussian Doppler broadening and a Lorentz pressure broadening component. It follows that it is especially also possible to take into account the influence of each individual hyperfine structure transition on the measurement results.

The representation of the emission profile of the primary radiation source chosen hereinbefore has the advantage that the influence of scattered light of the primary radiation source on the measurement result can be taken into account directly. Also this circumstance will improve the measurement results in comparison with the known method.

The method according to the present invention can be used in connection with a great variety of different atomizers known in the field of atomic absorption.

For example, a known graphite furnace with or without integrated platform can be used. In this case, the temperatures of the atomizer surface can be determined by pyrometric measurements at support points defined in the area of the atomizer wall and, where applicable, in the area of the integrated platform. For this purpose, the radiation intensity of the temperature radiation emitted by the components in question is measured and, finally, converted into a temperature. Details describing how such a temperature measurement can be carried out are disclosed e.g. in WO 94/23285.

In addition, for specific analytes to be detected, e.g. mercury, the method can also be used in connection with an experimental set-up including a quartz cell, which can be operated in a heated (e.g. for the hydride technique) as well as in an unheated (e.g. for the cold-vapour technique) condition. In the latter case, the temperature measurements are reduced to a measurement of the room temperature.

Further advantageous embodiments of the method according to the present invention result from the description of the preferred embodiments following hereinbelow as well as from the dependent method claims.

The method according to the present invention can be carried out by a device of the type mentioned at the beginning, which is characterized by a means for reconstructing the temperature field in the absorption volume on the basis of the surface temperatures determined, a means for determining absorption profiles with due regard to effects influencing the line profile of the analyte and with due regard to the reconstructed temperature field, a means for determining the position- and time-dependent numbers of particles of the absorbing atoms of the analyte on the basis of the position- and time-dependent measurements of the spectrometer and the absorption profiles determined, and a means for determining the time-dependent total number of particles of the absorbing atoms of the analyte on the basis of the position- and time-dependent numbers of particles.

This device according to the present invention can be further developed in an advantageous manner in accordance with the specific embodiments of the methods used. These advantageous further developments also result from the description of the preferred embodiments as well as from the dependent device claims.

BRIEF DESCRIPTION OF THE DRAWINGS

In the following, the present invention will be explained in detail on the basis of preferred embodiments shown in the drawing, in which.

DETAILED DESCRIPTION OF THE PREFERRED EMBODIMENT

Figure 1:
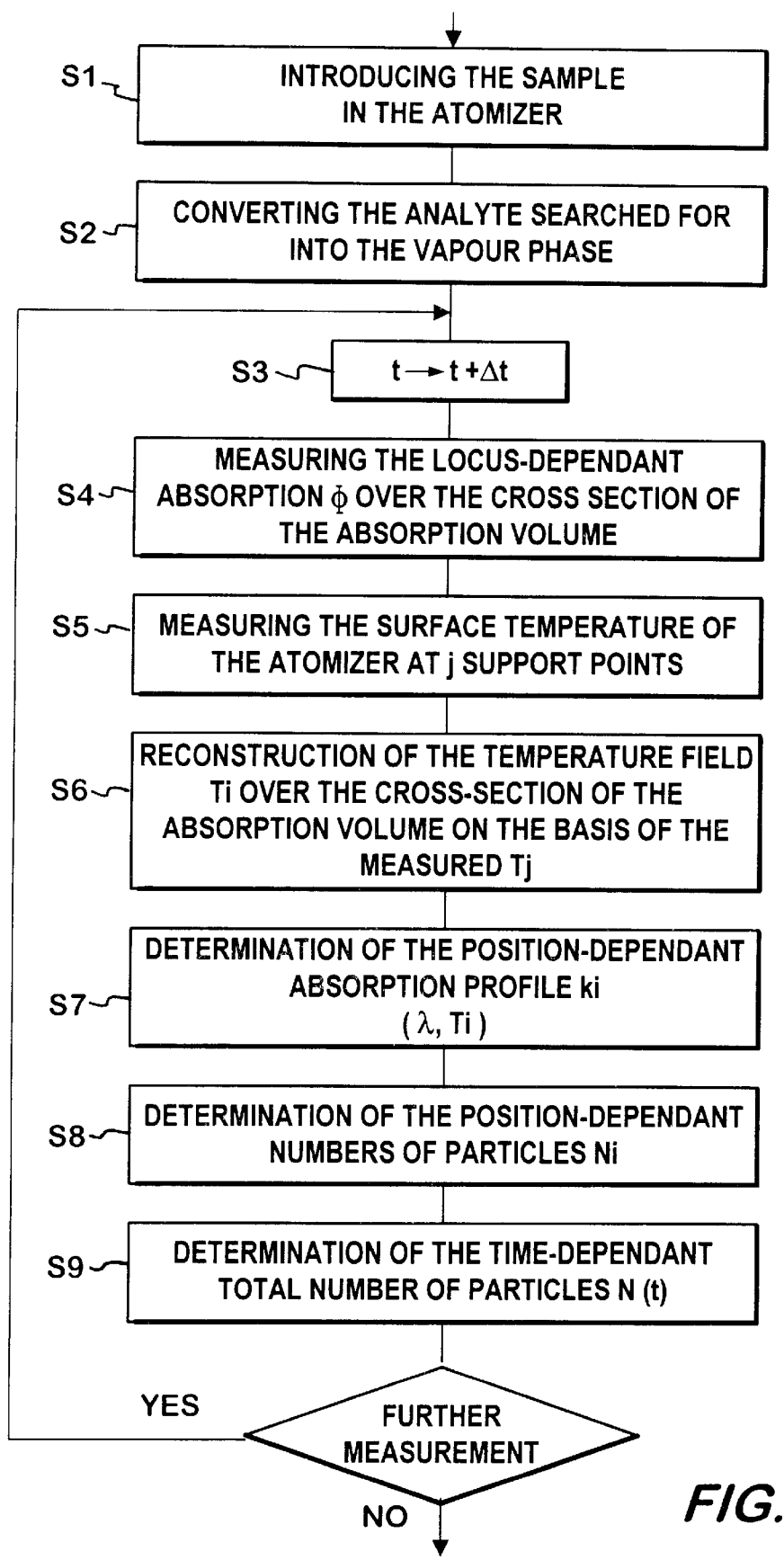
FIG. 1 shows a flow diagram for explaining the method according to the present invention.

FIG. 1 shows a flow chart for explaining the atomic absorption spectroscopy method according to the present invention.

In step S1, a sample to be examined is introduced in an atomizer.

The analyte searched for in this sample is converted into the vapour phase in step S2. If e.g. a graphite furnace is used, this conversion is effected by heating the furnace.

In addition to graphite furnaces, also other atomizers can be used in accordance with the analytes to be detected. Quartz tube cells permit, for example, a continuous or intermittent introduction of gaseous samples or aerosols with the aid of thermal, chemical or pneumatic gas or aerosol generators.

For a predetermined moment of time, which is determined in step S3, the measurement of the position-dependent atomic absorption is carried out. In so doing, the intensity $\Phi(X, t)$ of the radiation, which was emitted by the primary radiation source and which passed through the absorption volume and was, consequently, not absorbed by the atoms of the analyte, is measured. For measuring the position dependency, it will be expedient to discretize the cross-section of the absorption volume in dependence upon the detector used. In the preferred embodiment, the spatial information available at the exit slit of the monochromator is used for this purpose by projecting the image at the exit slit onto a linear array of photodiodes (PDA) or onto another suitable array of pixels (CCD detector) so that the intensity $\Phi_i$ in the absorption volume range i, which is imaged onto the i-th detector pixel, is measured by said i-th detector pixel. Depending on the structural design of the respective monochromator used, it is, of course, also possible to image the whole cross-section of the absorption volume onto a pixel array (CCD detector).

These position- and time-dependent measurements can be corrected by known background absorption methods.

In step S5, the surface temperature $T_j$ is measured at j predetermined support points of the atomizer. When a graphite furnace is used with or without an integrated platform, the support points are defined on the tubular wall or on the tubular wall and the integrated platform. At these support points, the surface temperature can be determined pyrometrically with the aid of the temperature radiation emitted by the heated tubular wall or by the heated tubular wall and the heated integrated platform. For this purpose, standard methods can be used, this type of methods being disclosed e.g. in WO 94/23285.

When the surface temperature of the graphite furnace components is determined pyrometrically, the determination of the thermal radiation intensity as well as the measurement of the intensity of the light which was emitted by the primary light source and which passed through the absorption volume can be carried out by a single detector array.

When a quartz cell is used instead of a graphite furnace, the surface temperature can be determined with the aid of conventional temperature measurement means, e.g. by contact measurements with a thermocouple or the like.

In step S6, the temperature field T(X,t) over the cross-section of the absorption volume is reconstructed from the j determined surface temperatures or support data $T_j$. In view of the fact that, as will explained hereinbelow, a position- and time-dependent number of particles (N(X,t) is to be determined on the basis of the reconstructed temperature field T(X,t) and the measured intensities $\Phi_i$, it will be expedient to discretize the temperature field also analogously to the measured intensities $\Phi_i$. Accordingly, i values of the temperature field $T_i$ are obtained in correspondence with the number i of the detector pixels. For reconstructing the temperature field $T_i$, from the support data ascertained, furnace-specific theoretical models, in which the design data of the respective furnace employed are taken into account, can be used.

Alternatively, it is also possible to determine the temperature field $T_i$ by comparing the determined support data with known temperature fields, i.e. with temperature fields which have, for example, been ascertained previously by a measurement, at the points corresponding to the j support points, i.e. at the points $T_{i=j}$. The various temperature fields, which are necessary for this purpose and which are also specific to the furnace in question, at the various time steps can be made available in a data base.

The measurement of temperature fields of various furnaces can be carried out by known methods. For example, the article "Spatially and temporally resolved gas phase temperature measurements in a Massmann-type graphite tube furnace using coherent anti-Stokes Raman Scattering" by Welz et al. in Spectrochimica Acta, Vol. 43 B, No. 9-11, pages 1187–1207, 1988, discloses how the longitudinal as well as the transverse field of a longitudinally heated graphite furnace can be determined by coherent anti-Stokes Raman Scattering. The temperature measurement in a transversely heated graphite tube is disclosed in "Das Aufheizverhalten von langsund quergeheizten Graphitrohröfen und die daraus resultierenden analytischen Eigenschaften für die Atomabsorptions-spektrometrie" by Sperling et al. in B.

Welz, CANAS' 95, Colloqium Analytische Atomspektroskopie, Überlingen, 1996.

In step S7, position-dependent absorption profiles $k_i$ are determined for the reconstructed temperature field $T_i$.

In this connection, $k_i(\lambda, T)$ can be given by the following theoretical model:

$$k(\lambda, T) = \sum_{k=1}^{n} b_k H_k(\lambda - \Delta\lambda_k + \Delta\lambda_s; a)$$

In this model, k is the k-th hyperfine structure component of the transition observed, $\Delta\lambda_k$ is the position of the k-th hyperfine structure component, $\Delta\lambda_s$ is the pressure broadening of the absorption profile relative to the emission profile, $H_k(\lambda; a)$ is the Voigt profile in which the Doppler broadening and the pressure broadening are taken into account, a is the ratio of the Doppler broadening and of the pressure broadening component for the absorption profile, and $b_k$ are the relative, standardized intensities of the individual hyperfine structure component transitions.

In this formula, Doppler broadening and pressure broadening effects are automatically taken into account by the Voigt profile $H_k(\lambda - \Delta\lambda_k + \Delta\lambda_s; a)$.

The absorption profile $k(\lambda, T)$ cannot only be determined by a theoretical model but also by way of experiment. With regard to the method according to the present invention, the experimentally determined absorption profiles are to be made available for a sufficiently large temperature range in this case. From these measurements, the absorption profiles $k_i$ can then be determined for given temperatures $T_i$.

In step S8, the position-dependent numbers of particles $N_i$ of the absorbing atoms are determined in the area of the absorption volume which is imaged onto the i-th detector pixel. These numbers of particles $N_i$ result from:

$$\int_{\Delta\lambda} d\lambda J(\lambda, X) e^{-k_i(\lambda) f N_i(t)} = 10^{-A_i(t)} \int_{\Delta\lambda} d\lambda J(\lambda, X) = \Phi_i(t)$$

Here $\lambda$ is the wavelength (integration variable), $\Delta\lambda$ is a spectral bandpass of the spectrometer used for measuring atomic absorption, $J(\lambda, X)$ is an a priori known emission profile of the primary radiation source used for measuring the atomic absorption, $k_i(\lambda)$ is the absorption profile corresponding to the i-th detector pixel and determined according to the statements made hereinbefore, f is the oscillator strength of a transition observed, $A_i(t)$ is the position and time-dependent extinction, and $\Phi_i(t)$ is the position- and time-dependent intensity of the radiation of the primary radiation source which passed through the absorption volume (i.e. which was not absorbed in the absorption volume), said intensity being determined by measurement.

The emission profile of the primary radiation source can in this connection be expressed by the following formula:

$$J(\lambda, X) = \sum_{k=1}^{n} b_k H_k\left(\frac{\lambda - \Delta\lambda_k}{\alpha}; a_e\right) + J_s(\lambda, X)$$

Here k is the k-th hyperfine structure component of the transition observed, $\Delta\lambda_k$ is the position of the k-th hyperfine structure component, $J_s(\lambda, X)$ is the profile of the spectral scattered light component, $H_k(\lambda; ae)$ is the Voigt profile, $a_e$ is the ratio of the Doppler broadening and of the pressure broadening component for the emission profile, $\alpha$ is the factor by which the emission profile is narrower than the absorption profile, and $b_k$ are the relative, standardized intensities of the individual hyperfine transitions. This representation especially also takes into account the influence of the scattered light component of the primary radiation source on the measurement.

Especially in cases where experimentally determined absorption profiles are made available, the determination of all i absorption profiles according to step S7 need not be carried out explicitly, but, upon calculating the i-th number of particles, the respective temperature-dependent absorption profile $k(\lambda, T)$ can directly be inserted in the above formula for calculating $N_i$.

In the last step S9, which is carried out for a given moment of time, the position- and time-dependent numbers of particles $N_i$ are, finally, used for determining the time-dependent total number of particles N(t) of the atoms of the examined analyte of the sample which absorb in the absorption volume.

This total number of particles N(t) can, for example, be determined by integration according to the formula $$N(t) = \sum_i N_i$$

After having carried out step S9, the measurement can either be finished or steps S4 to S9 can be repeated for another moment of time $t+\alpha t$.

The time-dependent total number of particles N(t) can, finally, be used for determining the concentration of the observed analyte in the sample to be examined. For this purpose, known methods can be used, such as the determination of the maximum of N(t) or the integration of the whole function N(t).

Figure 2:
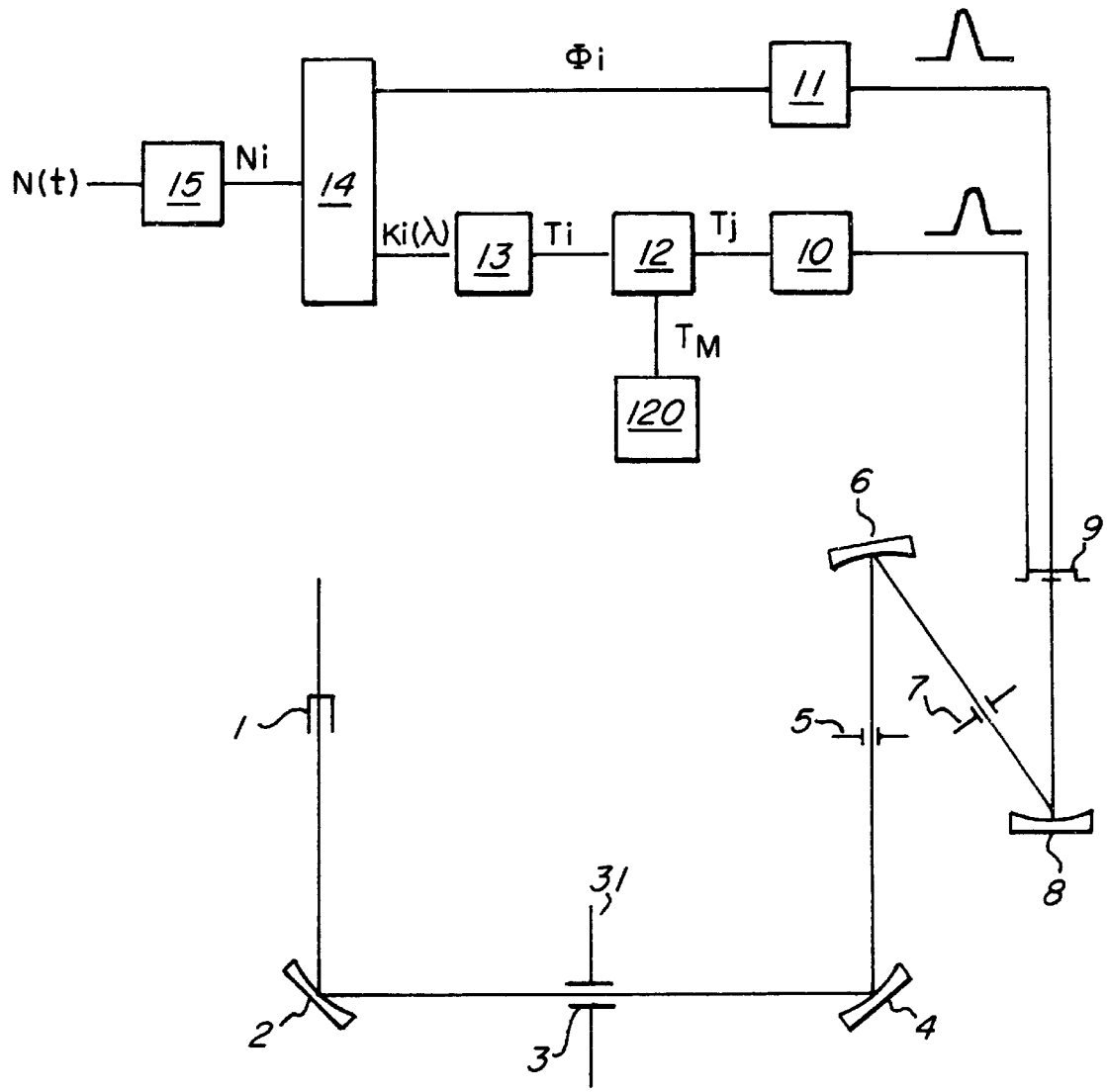
FIG. 2 shows a device for carrying out an atomic absorption spectroscopy according to an embodiment of the present invention.

FIG. 2 shows a device for carrying out an atomic absorption spectroscopy according to the method described hereinbefore.

Reference numeral 1 designates a primary radiation source. The radiation sources known from atomic absorption spectroscopy, such as a hollow-cathode lamp, an electrodeless discharge lamp, etc., can be used as a primary radiation source.

Reference numerals 2 and 4 stand for optical elements used for deflecting the radiation emitted by the primary radiation source.

Furthermore, the device shown includes a tubular atomizer 3. Known graphite furnaces with or without integrated platform, heated or unheated quartz tube cells, etc. can be used as atomizers.

In addition, the device according to FIG. 2 includes a monochromator consisting of an entrance slit 5, a grating 6 and an exit slit 7. By means of this monochromator, a spectral bandpass $\Delta\lambda$ is realized.

The monochromator is followed by a projection lens 8 projecting the image of the central radial cross-section 31 of the furnace onto the semiconductor detector 9 for evaluating the spatial information available.

The semiconductor detector 9 used is a detector array, e.g. a linear array or a matrix array. Detectors which are suitable to be used for this purpose are modern semiconductor detectors, such as a linear photodiode array or a CCD detector.

The semiconductor detector 9 is followed by an evaluation unit 11 which processes the signals of said semiconductor detector 9.

In the embodiment according to FIG. 2, components 9 and 11 define a spatially- and temporally-resolving spectrometer.

Figure 3:
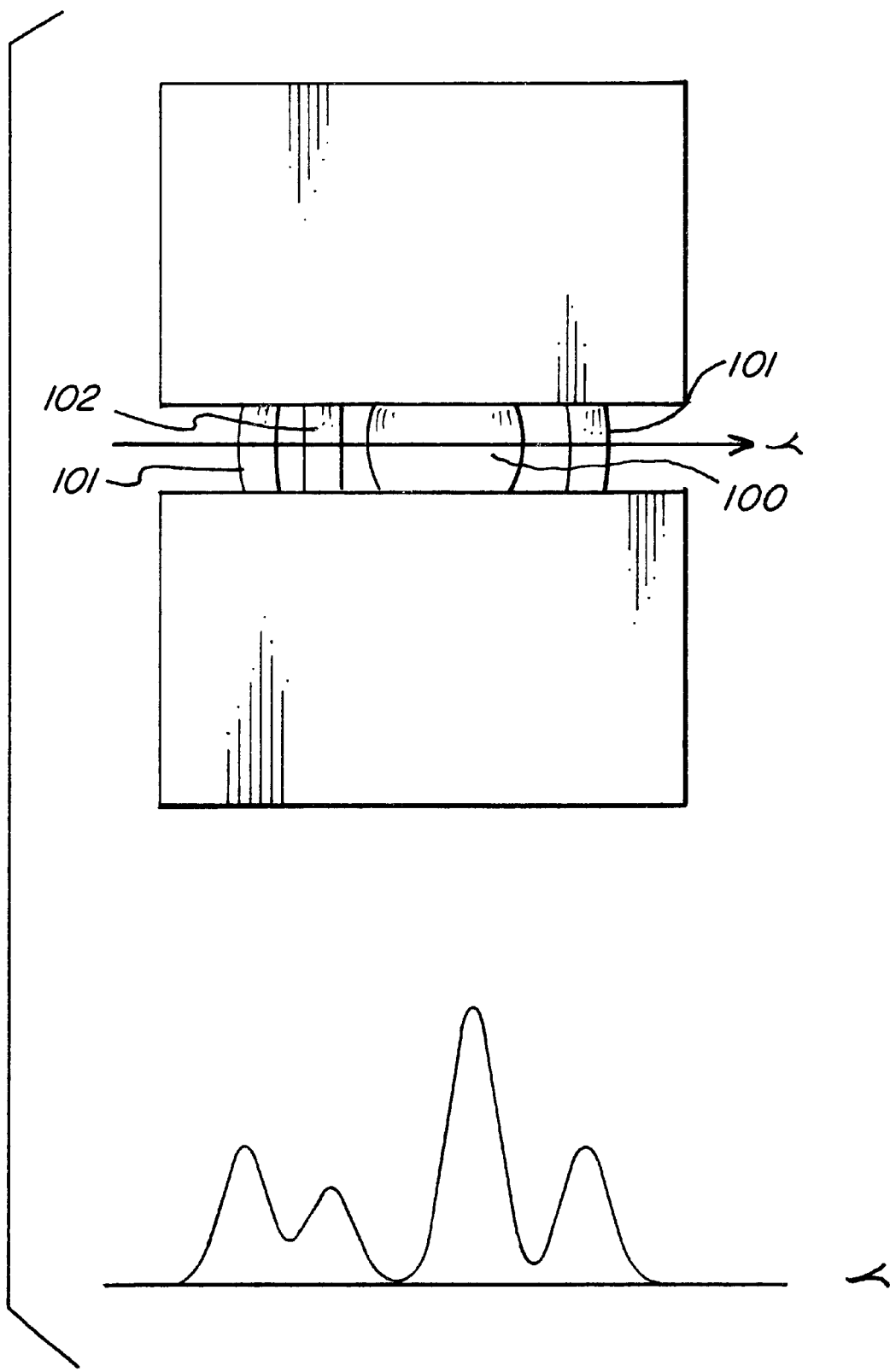
FIG. 3 shows a schematic view of an image at the exit slit of a monochromator used in the device according to FIG. 2, said image being projected onto the detector array.

FIG. 3 shows how the central radial cross-section 31 of a graphite furnace 3 with integrated platform is imaged onto the detector array 9 by means of the optical element 4, the monochromator 5, 6 and 7 and the projection lens 8. Below said representation, it is schematically shown which intensities are measured on various areas of the detector array.

In this schematic representation, the two outer peaks result from the temperature radiation of the furnace wall. The smaller one of the two central peaks is caused by the temperature radiation of the platform whose temperature is lower than that of the tubular wall. The highest peak in this schematic representation originates from the primary radiation source.

For a graphite furnace with integrated platform, which is the case shown, the individual pixels of the detector can be subdivided into three groups (cf. FIG. 3). The first group are pixels 100 which can have associated therewith respective areas of the atomization volume in the furnace. The second group comprises the pixels 101 of the detector array onto which the tubular furnace wall is imaged by means of the arrangement described. Finally, the group of pixels 102 consists of the pixels onto which the integrated platform of the graphite furnace 3 is imaged in an analogous fashion.

By means of the pixels 100, which each correspond to a specific area in the atomization volume of the furnace, the intensity of the radiation that passed through this area of the furnace, i.e. of the radiation which has not been absorbed by the analyte of the sample, is determined.

By means of the pixels 101 of the second group and the pixels 102 of the third group, the intensity of the temperature radiation of the heated furnace wall and of the furnace platform can be determined.

The electric signals outputted by the pixels 100 of the detector array are supplied to a means 11 for determining the intensity of the radiation which has been emitted by the radiation source 1 and which has passed through the absorption volume.

The signals of the pixels 101 and 102 are supplied to a means 10 for determining the surface temperature of the atomizer 3. Said means 10 especially determines the surface temperature $T_j$ at predetermined support points j in the area of the furnace wall and of the integrated platform.

These temperatures $T_j$ at said predetermined support points j are supplied to a reconstruction means 12. This reconstruction means 12 determines from the measurements at the support points the temperature field $T_i$ which is radial with regard to the longitudinal axis of the furnace and which has been discretized according to the procedure described hereinbefore.

As has already been explained hereinbefore, furnace-specific theoretical models, in which the design data of the respective furnace employed play a part, can be used for this purpose.

Alternatively, the temperature field can also be determined by comparing the temperatures measured at the support points with a priori measured temperature fields. The various temperature fields $T_M$ required for this purpose at the various time steps can be stored in a data base 120. This permits fast access of the reconstruction means 12 to the various temperature fields for carrying out the comparison. In this data base 120, it is also possible to store corresponding temperature fields for different furnaces.

The position-dependent temperature field $T_i$ reconstructed in said means 12 is supplied to a means 13 for determining the absorption profiles with due regard to Doppler broadening and pressure broadening effects and the reconstructed temperature field.

This means 13 can be provided in the form of a microcomputer in which the position- and time-dependent temperature profiles are determined for specific temperatures T according to the formula $$k(\lambda, T) = \sum_{k=1}^{n} b_k H_k(\lambda - \Delta\lambda_k + \Delta\lambda_s; a)$$

which has been discussed hereinbefore.

These position- and time-dependent temperature profiles $k_i(\lambda, T)$ are transmitted from said means 13 to a means 14 for determining position- and time-dependent particle numbers of the absorbing atoms of the analyte. Together with the measured, discretized intensities $\Phi_i$ of the radiation of the primary radiation source which passed through the absorption volume (but which was not absorbed), i.e. the intensities $\Phi_i$ corresponding to said i detector pixels, said means 14 determines the position- and time-dependent particle numbers $N_i$ according to the formula $$\int_{\Delta\lambda} d\lambda J(\lambda, X) e^{-k_i(\lambda)fN_i(t)} = 10^{-A_i(t)} \int_{\Delta\lambda} d\lambda J(\lambda, X) = \Phi_i(t)$$

which has been discussed hereinbefore.

From these position-dependent particle numbers $N_i$ the time-dependent total number of particles N(t) of the absorbing atoms in the analyte can then be determined by an integration means 14. For diagnostic purposes, it is also possible to evaluate the local particle numbers and to show them in a representation.

Alternatively to the above-described graphite furnace provided with an integrated platform, it is also possible to use a graphite furnace without an integrated platform.

In this case, the above-mentioned pixels 102 belong to the first group and can, consequently, be associated with respective areas in the atomization volume in the furnace. In addition, in view of the radial symmetry of the tubular furnace, this embodiment permits a reduction of the number of support points at which the surface temperature is determined by means of pyrometry.

When a graphite furnace without integrated platform is used, the reconstruction means is to be adapted in such a way that the position-dependent temperature field can be reconstructed from the measured tubular wall temperatures. Analogously to the furnace with integrated platform, either a theoretical model or a priori measurements of the temperature field of the furnace used can be assumed in this respect.

In addition to graphite furnaces, it is also possible to use in dependence upon the analytes to be examined—heatable furnaces made of metal, or silica glass tubular atomizers, which can be operated either in an unheated condition for cold-vapour techniques or such that they are heated externally by flames or electrically heated.

In this case, the means 10 for determining the temperature of the atomizer is constructed such that it measures the surface temperature in a suitable manner. Hence, said means 10 is no longer connected to the detector array 9, but to a conventional temperature sensor. In this connection, only a few measurements will normally be necessary for achieving a sufficiently exact determination of the surface temperature of the atomizer. Furthermore, also the reconstruction means 12 will be less complicated in this case, since the radial temperature gradients over the cross-sectional area of the furnace are, comparatively, small.

Figure 4:
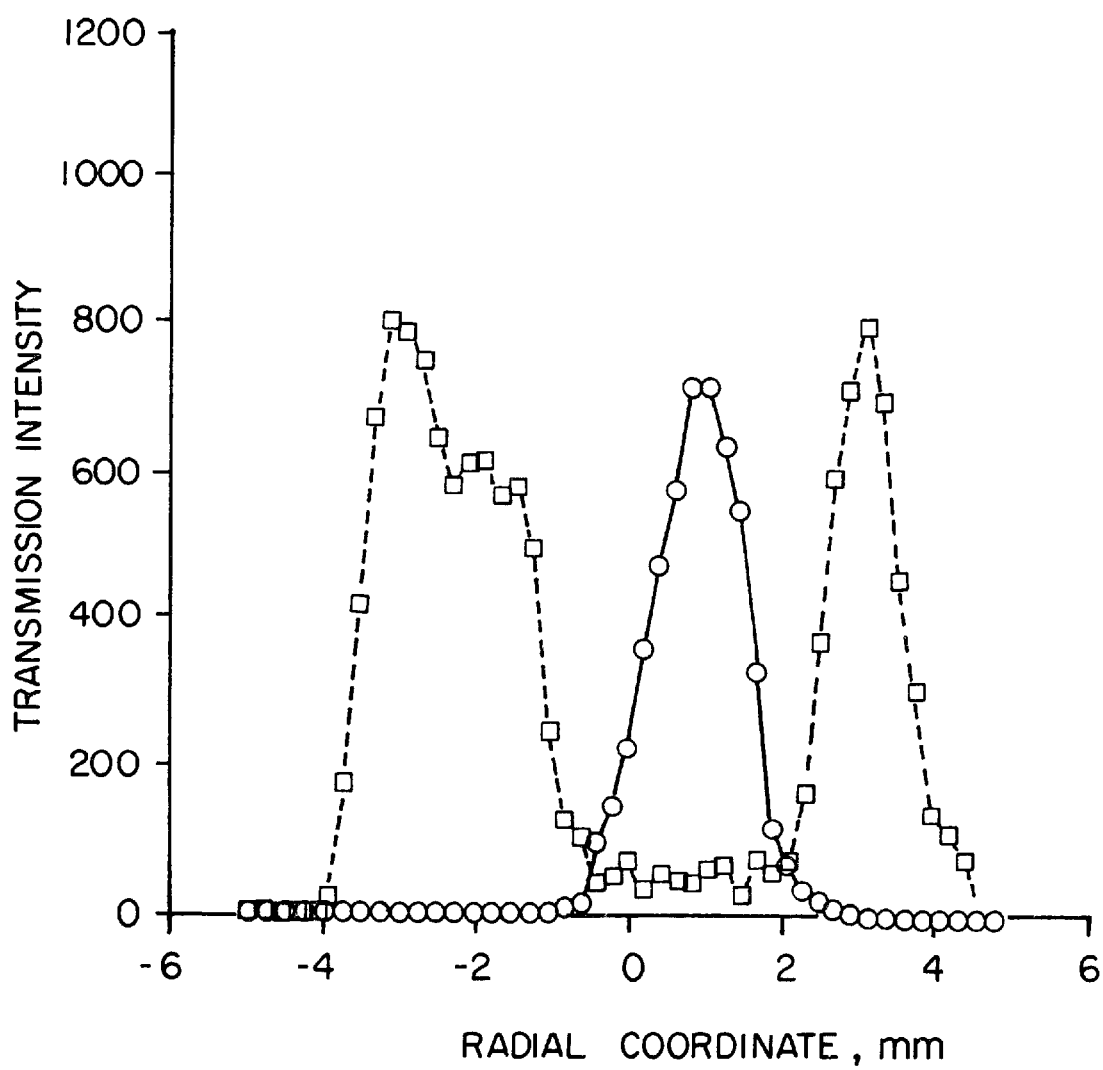
FIG. 4 shows spatially resolved radiation intensities of various sources, such as the hot wall of the atomizer, the hot platform and the primary radiation source.

FIG. 4 shows a quantitative representation of the intensity profile on various areas of the detector array, said intensity profile being schematically outlined in FIG. 3. The solid squares in FIG. 4 stand for the measuring points of the temperature radiation intensity of the furnace. The solid circles represent the radiation intensity of the primary radiation source, which is a hollow-cathode lamp in this case. Analogously to FIG. 3, the two outer peaks result from the temperature radiation of the furnace walls. The smaller one of the two central peaks results from the temperature radiation of the platform and the higher one of said two peaks represents the radiation intensity of the hollow-cathode lamp.

What is claimed is:

1. A method for atomic absorption spectroscopy of an analyte which is contained in a sample to be analyzed and which is converted into free atoms in an absorption volume of an atomizer, comprising the steps of:
    (a) position- and time-dependent measuring of the atomic absorption over a cross-section of the absorption volume,
    (b) simultaneous determination of surface temperatures of the atomizer, characterized by the steps of:
    (c) reconstructing a temperature field over the cross section of the absorption volume on the basis of the surface temperatures determined,
    (d) determining position- and time-dependent numbers of particles of the absorbing atoms of the analyte on the basis of the measurements of the position- and time-dependent atomic absorption and an absorption profile that has been theoretically determined, said absorption profile taking into account effects influencing a line profile of the analyte and the reconstructed temperature field, and
    (e) determining the time-dependent total number of the absorbing atoms of the analyte on the basis of the position- and time-dependent numbers of particles.

2. A method according to claim 1, wherein the position- and time-dependent number of particles N (X, t) is determined from:

$$\int_{\Delta\lambda} d\lambda J(\lambda, x) e^{-k(\lambda,T) f N(x,t)} = 10^{-A(x,t)} \int_{\Delta\lambda} d\lambda J(\lambda, x) = \Phi(x, t)$$

where:
  $\lambda$: is the wavelength (integration variable),
  $\Delta\lambda$: is a spectral bandpass of the spectrometer used for measuring the atomic absorption
  $J(\lambda, X)$: is an a priori emission profile of the primary radiation source used for measuring the atomic absorption
  $k(\lambda, T)$: is an a priori temperature-dependent absorption profile for the measured temperature T,
  f: is the oscillator strength of a transition observed,
  $A(X,t)$: is the position- and time-dependent extinction,
  $\Phi(X, t)$: is the position- and time-dependent intensity of the radiation of the primary radiation source which passed through the absorption volume, said intensity being determined by measurement.

3. A method according to claim 2, wherein the emission profile $J(\lambda, X)$ and the temperature-dependent absorption profile $k(\lambda, T)$ are a priori determined from:

$$J(\lambda, X) = \sum_{k=1}^{n} b_k H_k\left(\frac{\lambda - \Delta\lambda_k}{\alpha}; a_e\right) + J_s(\lambda)$$

$$k(\lambda, T) = \sum_{k=1}^{n} b_k H_k(\lambda - \Delta\lambda_k + \Delta\lambda_s; a)$$

where:
  k: is the k-th hyperfine structure component,
  $\Delta\lambda_k$: is the position of the k-th hyperfine structure component,
  $J_s(\lambda, X)$: is the profile of the spectral scattered light component,
  $\Delta\lambda_s$: is the pressure broadening of the absorption profile relative to the emission profile,
  $H_k$: is the Voigt profile in which the Doppler broadening and the pressure broadening of the respective spectral lens are taken into account,
  $a, a_e$: is the ratio of the two broadening components for the absorption profile and for the emission profile,
  $\alpha$: is the factor by which the emission profile is narrower than the absorption profile,
  $b_k$: are the relative standardized intensities of the hyperfine transitions.

4. A method according to claim 1, whereing the temperature field is reconstructed on the basis of surface temperatures, which are determined at support points depending on the atomizer used, and on the basis of a model depending on said atomizer.

5. A method according to claim 4, wherein the atomizer used is a graphite furnace.

6. A method according to claim 5 wherein the graphite furnace comprises a tubular wall and wherein the support points are provided adjacent the tubular wall.

7. A method according to claim 5, wherein a graphite furnace with integrated platform is used.

8. A method according to claim 7, wherein additional support points are provided adjacent the integrated platform.

9. A method according to claims 4, wherein the surface temperatures at the support points are measured by pyrometry.

10. A method according to claim 9, wherein the surface temperatures at the support points are measured by means of a detector used for measuring the atomic absorption.

11. A method according to claim 4, wherein the atomizer used is a heated or unheated quartz cell.

12. A method according to claim 11, wherein the surface temperature of the atomizer is determined by means of at least one temperature measurement which is carried out adjacent the surface.

13. A method according to claim 1, wherein the time-dependent total number is determined by integration of the position- and time-dependent numbers of particles.

14. A device for carrying out atomic absorption spectroscopy, comprising:
  a radiation source (1),
  an atomizer (3) which provides an absorption volume,
  a position- and time-resolving spectrometer (9,11) for measuring over a cross-section of the absorption volume light which has been emitted by the radiation source and which has passed through the absorption volume,
  a means (9,10) for determining surface temperatures of the atomizer, characterized by:

a means (12) for reconstructing a temperature field over the cross-section of the absorption volume on the basis of the surface temperatures determined, a means (13) for theoretically determining absorption profiles, said absorption profiles taking into account effects influencing a line profile of the analyte and the reconstructed temperature field, a means (14) for determining the position- and time-dependent numbers of particles of the absorbing atoms of the analyte on the basis of the position- and time-dependent measurements of the spectrometer and the theoretically determined absorption profiles, and a means (15) for determining the time-dependent total number of particles of the absorbing atoms of the analyte on the basis of the position- and time-dependent numbers of particles.

15. A device according to claim 14, wherein the means (14) for determining the position- and time-dependent numbers of particles id adapted in such a way that the position- and time-dependent numbers of particles $N(X, t)$ are determined from:

$$\int_{\Delta\lambda} d\lambda J(\lambda, x) e^{-k(\lambda, T)fN(x,t)} = 10^{-A(x,t)} \int_{\Delta\lambda} d\lambda J(\lambda, x) = \Phi(x, t)$$

where:
$\lambda$: is the wavelength (integration variable),
$\Delta\lambda$: is a spectral bandpass of the spectrometer used for measuring the atomic absorption
$J(\lambda, X)$: is an a priori emission profile of the primary radiation source used for measuring the atomic absorption
$k(\lambda, T)$: is an a priori temperature-dependent absorption profile for the measured temperature T,
f: is the oscillator strength of a transition observed,
$A(X,t)$: is the position- and time-dependent extinction,
$\Phi(X, t)$: is the position- and time-dependent intensity of the radiation of the primary radiation source which passed through the absorption vole, said intensity being determined by measurement.

16. A device according to claim 15, wherein said means for determining the absorption profile is adapted in such a way that the position- and time-dependent absorption profile $k(\lambda, T)$ is determined from:

$$k(\lambda, T) = \sum_{k=1}^{n} b_k H_k(\lambda - \Delta\lambda_k + \Delta\lambda_s; a)$$

and the emission profile $J(\Delta, X)$ is described by $$J(\lambda, X) = \sum_{k=1}^{n} b_k H_k\left(\frac{\lambda - \Delta\lambda_k}{\alpha}; a_e\right) + J_s(\lambda, X)$$

where: is the k-th hyperfine structure component,
k: is the position of the k-th hyperfine structure component,
$J_s(\lambda, X)$: is the profile of the spectral scattered light component,
$\Delta\lambda_s$: is the pressure displacement of the absorption profile relative to the emission profile,
$H_k$: is the Voight profile in which the Doppler broadening and the pressure broadening of the respective spectral lens are taken into account,
$a, a_e$: is the ratio of the two broadening components for the absorption profile and for the emission profile
$\alpha$: is the factor by which the emission profile is narrower than the absorption profile
$b_k$: are the relative standardized intensities of the hyperfine structure transitions.

17. A device according to claim 14, wherein the means for measuring the surface temperature of the atomizer (3) is adapted in such a way that the surface temperature can be determined at support points depending on the atomizer used.

18. A device according to claim 17, wherein the atomizer (3) is a furnace made of graphite or metal.

19. A device according to claim 18 wherein the furnace comprises a tubular wall and wherein the support points for determining the surface temperature are provided adjacent the tubular wall.

20. A device according to claim 18, wherein the graphite furnace is provided with an integrated platform.

21. A device according to claim 20, wherein additional support points are provided adjacent the integrated platform.

22. A device according to claim 17, wherein a pyrometer means (10) is provided for measuring the surface temperatures at the support points.

23. A device according to claim 22, wherein the pyrometer means and the spatially- and temporally-resolving spectrometer means have a common detector (9).

24. A device according to claim 23, wherein the common detector (9) comprises a semiconductor detector array.

25. A device according to claim 17, wherein the atomizer (3) is a heated or unheated cell of quartz or ceramic material.

26. A device according to claim 25, wherein the means for determining the surface temperature of the atomizer is a means for contact measurement.

27. A device according to claims 14, wherein the means (15) for determining the total number of particles of the absorbing atoms of the analyte is an integration device for integrating the position- and time-dependent numbers of particles.

* * * * *